US005733754A

United States Patent [19]
Wisdom et al.

[11] Patent Number: 5,733,754
[45] Date of Patent: Mar. 31, 1998

[54] ENZYME AND ITS USE IN PREPARING (S)-PIPECOLIC ACID

[75] Inventors: Richard Anthony Wisdom, Cambridge; Caroline Susan Lee, Cambridgeshire; Paul Maurice Ricaud, Cambridge, all of United Kingdom

[73] Assignee: Chiroscience Limited, Cambridge, United Kingdom

[21] Appl. No.: 615,193

[22] PCT Filed: Oct. 14, 1994

[86] PCT No.: PCT/GB94/02259

§ 371 Date: Apr. 8, 1996

§ 102(e) Date: Apr. 8, 1996

[87] PCT Pub. No.: WO95/10604

PCT Pub. Date: Apr. 20, 1995

[30] Foreign Application Priority Data

Oct. 15, 1993 [GB] United Kingdom ............... 9321325

[51] Int. Cl.$^6$ ............... C12P 13/04; C12P 17/12; C12N 9/78; C12N 1/20; C12N 11/00
[52] U.S. Cl. ............... 435/106; 435/122; 435/174; 435/280; 435/227; 435/252.1
[58] Field of Search ............... 435/136, 228, 435/822, 829, 68.1, 4, 252.1, 280, 129, 106, 122, 174, 227

[56] References Cited

U.S. PATENT DOCUMENTS 5,120,652 6/1992 Groeger et al. ............... 435/228
5,219,741 6/1993 Groeger et al. ............... 435/107

FOREIGN PATENT DOCUMENTS 0 416 282 3/1991 European Pat. Off. .

OTHER PUBLICATIONS

K. Mochizuki et al., "Simultaneous Production of D–Pipecolic Acid and L–α–Aminoadipic Acid from DL–Pipecolic Acid Using A Microoragnism", *Agric. Biol. Chem.* 52(5): 1113–1116 (1988).

E. Toone et al., "Enzymes in organic synthesis. 40.[1] Evaluation of the enantioselectivity of the pig liver esterase catalyzed hydrolyses of recemic piperidine carboxylic acid esters", *Can. J. Chem.* 65: 2722–2726 (1987).

*Chemical Abstracts* 110(9): 506 (1989), abstract 73875p.

*Primary Examiner*—Mary E. Mosher
*Attorney, Agent, or Firm*—Foley & Lardner

[57] ABSTRACT

An enzyme is provided which has acylase activity capable of hydrolyzing N-acetyl-(R,S)-pipecolic acid stereoselectively to give (S)-pipecolic acid, wherein this activity is greater than that on N-acetyl-S-proline, at pH 7.5, 25° C., and substrate concentration 20 g/l, in 75 mM Tris buffer. The enzyme is obtainable from the species of *Alcaligenes denitrificans* deposited as NCIMB 40587. A microorganism having therein the enzyme also is provided, as is a process for preparing (S)-pipecolic acid comprising contacting a mixture of enantiomers of an N-acyl-pipecolic acid with the enzyme or microorganism.

11 Claims, No Drawings

ENZYME AND ITS USE IN PREPARING (S)-PIPECOLIC ACID

FIELD OF THE INVENTION

This invention relates to an enzyme and its use, for example in preparing (S)-pipecolic acid.

BACKGROUND OF THE INVENTION (S)-Pipecolic acid is an intermediate in the preparation of levobupivacaine, the less cardiotoxic enantiomer of the analgesic and anaesthetic agent bupivacaine. Various methods for preparation of this synthon are known.

Ng-Young-Chen et al, J. Org. Chem. 59:2075–81 (1994), describe the resolution of pipecolic acid esters using *Aspergillus niger* lipase. Low ee (S)-pipecolic acid was produced. An enhancement in enantioselectivity could be obtained through partial purification of the enzyme, but in this case a maximum ee of only 93% was obtained. Use of N-acyl-pipecolic acid ester substrates resulted in no improvement in enantioselectivity.

Toone and Jones, Can. J. Chem. 65:2722–6 (1987), report on the utility of pig liver esterase to carry out similar pipecolic acid ester resolutions ee values were found to be less than 50%.

Mochizuki et al, Agric. Biol. Chem. 52:1113–6 (1988), describe the use of an Alcaligenes strain to selectively metabolise (S)-pipecolic acid to accumulate (S)-α-aminoadipic acid and leave (R)-pipecolic acid. This is not suitable for (S)-pipecolic acid production and results in loss of a significant proportion of the (S)-α-aminoadipic acid due to its further metabolism.

An alternative approach has been described by Huh et al, Biosci. Biotech. Biochem. 56:2081–2 (1992), who used D-amino-acid oxidase from porcine kidney to selectively oxidise (R)-pipecolic acid to $\Delta^1$-piperidine-2-carboxylic acid and leave (S)-pipecolic acid as product. The $\Delta^1$-piperidine-2-carboxylate could be recycled to (R),(S)-pipecolic acid in the reaction mixture through the addition of sodium borohydride, but at elevated concentrations this was inhibitory to the oxidase enzyme. Industrial use of this system would additionally be restricted by the cost, poor availability and low stability of the enzyme.

The use of amino acylases to resolve N-acylamino-acids is well established. Verkhovskaya et al, Russian Chemical Reviews 60:1163–79 (1991), review this and other technologies for producing amino-acids. In particular, they disclose the use of acylases from *Aspergillus sp.*, *Bacillus sp.* or porcine kidney for the resolution primary amino-acids. However, such enzymes do not have activity against secondary N-acylamino-acids.

EP-A-0416282 discloses a N-acylamino-acid acylase, to produce (S)-proline. The addition of substrate during the fermentation was necessary in order to obtain the required activity. N-acyl-(S)-proline (the primary substrate) is expensive and will be consumed during the fermentation. The activity of the enzyme on N-acyl-pipecolic acid was very low, at less than 5% of its activity on N-acetyl-proline, i.e. N-acyl-pipecolic acid compounds are very poor substrates for the enzyme.

SUMMARY OF THE INVENTION

A microbial N-acyl-pipecolic acid acylase has been found, that has good potential for long term re-use, that does not require addition of inducer for expression of activity, and that has activity on N-acyl-pipecolic acid at least comparable to its activity on N-acyl-proline. Its preferred activities are based on Example 6 herein. Specifically, the enzyme preferably has acylase activity capable of hydrolysing N-acetyl-(R,S)-pipecolic acid stereoselectively, to give (S)-pipecolic acid, wherein said activity is greater than that on N-acetyl-S-proline, at pH 7.5, 25° C., and substrate concentration 20 g/l, in 75 mM Tris buffer, and more preferably also has activity on N-acetyl-(R,S)-alanine that is at least 40%, preferably at least 50%, of the activity on N-acetyl-(S)-proline under the foregoing conditions.

In addition, it is surprisingly found that the novel enzyme has activity on primary N-acyl-amino-acids. Thus both aromatic and aliphatic amino-acids such as phenylalanine and alanine may be resolved using the enzyme to give the (S) amino acid with an ee of at least 95%, and often greater than 98%. This broad activity range is unusual and has not been described for other N-acylamino-acid acylases.

This enzymatic activity is available in a strain of *Alcaligenes denitrificans*, identified as A2LA3, that has been deposited under the terms of the Budapest Treaty at the National Collection of Marine Bacteria, 23 St. Machar Drive, Aberdeen, Scotland, United Kingdom AB2 1RY on 14 Sep., 1993. The accession number is NCIMB 40587.

DESCRIPTION OF THE INVENTION

The novel enzymatic activity can be isolated by growth enrichment on N-acetyl-(S)-phenylalanine, and screening. The isolated activity can be used to convert racemic or optically-enriched N-acyl-pipecolic acid to (S)-pipecolic acid, under conventional conditions, using conventional media. The organism can be handled in conventional manner; in particular, it can be satisfactorily used on a large scale. The unconverted (R)-N-acyl-pipecolic acid can be readily separated from the desired product and, if desired, racemised. The desired product can be converted to levobupivacaine or an analogue thereof, e.g. the corresponding enantiomer of ropivacaine, by conventional methodology.

The following Examples illustrate the invention.

EXAMPLE 1

Selection

Numerous isolates were selected from soil by enrichment in a medium containing N-acetyl-S-phenylalanine as the sole source of carbon and energy. This was carried out by adding a small amount of soil to the enrichment medium (Table 1) and allowing growth to proceed over 48 hr. Secondary flasks, containing a similar medium, were then inoculated at 1% (v/v) from the primary flasks. After 72 hr growth, samples from the secondary cultures were diluted and spread-plated onto nutrient agar supplemented with 1% (w/v) glucose, pH 7. Colonies were isolated after 48 hr growth at 25° C.

To establish which isolate had the most desirable properties for the current process, liquid cultures of each of the isolates were grown and subsequent biotransformations against the appropriate substrate were carried out according to the following procedure. Cells of each isolate were grown in 50 ml medium (Table 2), in 250 ml Erlenmeyer flasks shaken at 300 rpm with a 25 mm (1 inch) throw, for 24 hr at 25° C. The cells were harvested by centrifugation (1200 g, 15 mins) and resuspended to their original harvest volume in deionized water. The suspensions were sonicated for 5 mins (10 seconds off, 10 seconds on cycles) at an amplitude of 16 μm in a Soniprep 150, and the cell debris removed by centrifugation as above.

The sonicate supernatants were then used in the following biotransformation reactions. To 1 ml of the sonicate supernatants, 1 ml of 40 g/l solution of N-acetyl-rac-pipecolate, pH 7, was added in the presence of 0.02% sodium azide. The biotransformation reaction mixtures were incubated with shaking for 48 h at 25° C., after which samples were removed and analysed by HPLC. HPLC analysis was done using a 15 cm Hichrom S50DS2 column with an isocratic mobile phase of 30% methanol:70% 10 mM potassium phosphate buffer, pH 3, at a flow rate of 1 ml/min. The injection volume was 20 µl and the detection was at 240 nm, total run time was 10 minutes. Prior to loading on to the column, the sample was diluted 20-fold in the HPLC mobile phase and centrifuged. The analyses as shown by this procedure provided values of residual substrate concentrations. A substrate control was run in parallel with the sample reactions.

On the basis of the extent of hydrolysis of the substrate, one isolate in particular was chosen for further study. The HPLC data revealed that, under the above reaction conditions, the isolate identified as A2LA3 achieved 45.2% hydrolysis of the substrate within 48 hours. Further analysis of the pipecolic acid produced showed it to have an ee of 99% towards the S-enantiomer.

This result was determined by derivatization and HPLC resolution on a Chiracel OD column using the following procedure. 20 ml of biotransformation mixture was rotary-evaporated to 5 ml. Conc. HCl was added until a pH of 2 was achieved and NaCl added to saturation.

Extraction of residual substrate was performed by mixing the above solution with 3×2 volumes n-butanol; the top organic layer was removed and discarded, and the aqueous layer was rotary-evaporated to dryness. To the dried sample approximately 2 ml methanol was added together with 50 µl concentrated HCl and the mixture heated at 90° C. in a dry block for 3 hours. The methanol was removed by rotary-evaporation; 2 ml dichloromethane plus 50 µl triethylamine were added together with 50 µl of benzyl chloroformate and the reaction allowed to proceed at ambient temperature for 15 mins. The mixture was washed with 2 volumes of deionized water and the top aqueous layer discarded. Anhydrous $MgSO_4$ was added to the dichloromethane layer which was then removed from the $MgSO_4$, and rotary-evaporated. The residue was taken up in 2 ml of 100% isopropyl alcohol (IPA). The sample was diluted to 1:10 in IPA and analysed by HPLC. A 25 cm Chiracel OD column (Cat. No. 7195-00, J. T. Baker, Reading) was used with a mobile phase of 10% IPA in heptane. The flow rate used was 1 ml/min with a run time of 20 minutes and detection at 210 nm.

As a result of the extent of hydrolysis of the substrate and the high % ee achieved by the isolate A2LA3, it was chosen as the most desirable strain isolated for the current process.

TABLE 1

|  | g/l |
| --- | --- |
| $(NH_4)_2SO_4$ | 1 |
| $KH_2PO_4$ | 5 |
| $MgSO_4.7H_2O$ | 0.1 |
| $CaCl_2.2H_2O$ | 0.05 |
| Trace elements | 50 µl/l |
| N-acetyl-L-Phenylalanine | 5 |
| pH | 7.0 |
| Trace Element Solution | |
| $CaCl_2.2H_2O$ | 3.6 |
| ZnO | 2.0 |
| $CuCl_2.2H_2O$ | 0.85 |

TABLE 1-continued

|  | g/l |
| --- | --- |
| $Na_2MoO_4.2H_2O$ | 4.8 |
| $MnCL_2.4H_2O$ | 2.0 |
| $FeCL_3.6H_2O$ | 5.4 |
| $H_3BO_3$ | 0.3 |
| $CoCl_2.6H_2O$ | 2.4 |
| Concentrated HCl (35%) | 250 ml |

TABLE 2

|  | g/l |
| --- | --- |
| $(NH_4)SO_4$ | 1 |
| $KH_2PO_4$ | 5 |
| $MgSO_4.7H_2O$ | 0.1 |
| $CaCl_2.2H_2O$ | 0.05 |
| Trace elements | 50 µl/l |
| Glucose | 5 |
| N-acetyl-rac-Phenylalanine | 5 |
| Yeast Extract | 2 |
| pH | 7.0 |

EXAMPLE 2

Use of Inducer

It has been observed by other workers that an inducer must be added to the fermentation medium to obtain N-acyl-amino-acid acylase activity. This adds to the cost of producing the enzyme. Flask cultures were set up to determine the requirement for an inducer. Medium used was similar to that described in Table 1, except that the N-acetyl-L-phenylalanine was omitted, 1 g/l yeast extract was added and the following 4 variations were set up.

Flask 1: An additional 5 g/l yeast extract added

Flask 2: N-acetyl-(S)-proline added to 5 g/l

Flask 3: N-acetyl-(R,S)-pipecolic acid added to 5 g/l

Flask 4: Glucose added to 5 g/l

The final pH of all flasks was adjusted to pH 7.0 and a total of 50 ml added to 500 ml conical flasks. Following inoculation, the flasks were incubated at 25° C. with shaking for 19 hours. The cells were then collected by centrifugation, resuspended in 10 mM phosphate buffer, pH 7 and lysed by sonication. The released enzyme extract was then used in a 24 hour biotransformation of 20 g/l N-acetyl-(R,S)-pipecolic acid. The results obtained are shown in Table 3.

TABLE 3

| Additive | Volumetric Activity (U/ml) | Specific (U/mg protein) |
| --- | --- | --- |
| Yeast Extract | 0.015 | 0.028 |
| N-acetyl-(S)-proline | 0.042 | 0.033 |
| N-acetyl-(R,S)-pipecolic acid | 0.017 | 0.086 |
| Glucose | 0.00 | |

1U = release of 1 µmole pipecolic acid per minute

Best total activity was obtained in the flask grown on N-acetyl-proline, however this was due to the greatly increased growth obtained in this flask. The specific activity of the cell extract shows a similar specific activity with the extract from yeast extract-grown culture. Thus, provided similar growth could be obtained in a fermenter, as might be expected with pH control, there is minimal advantage in the use of N-acetyl-proline. As expected, the flask containing glucose showed no N-acetyl-pipecolic acid acylase activity, presumably due to catabolite repression. The flask containing (N)-acetyl-(R,S)-pipecolic acid showed poor growth, however the cell extract showed a high specific activity.

The results suggest that for maximal specific activity the addition of a poorly metabolisable inducer, such as N-acetyl-(R,S)-pipecolic acid, may be desirable. However, good activity can still be obtained without a specific inducer being added.

EXAMPLE 3
Large Scale Fermentation

A. *denitrificans* (NCIMB 40587) was grown to 500 l using the following procedure. A colony from a nutrient agar plate was inoculated into a 2 l flask containing 500 l seed media. This was then grown with shaking at 25° C. for 24 hours. The seed medium used is shown in Table 4. Following growth, the entire culture was inoculated into a 750 l fermentation vessel containing 500 l of production medium (also shown in Table 4). Growth was then continued at 25° C., pH 7.0 ($H_3PO_4$ for control) and DOT>30% air saturation until readily metabolisable carbon sources had been fully utilised, as indicated by a rapid drop in the culture oxygen demand. This typically took about 26 hours. At this point, the air was turned off and the temperature set point adjusted to 15° C. After conditions had stabilized the cells were harvested using a continuous disk stack centrifuge to give 45 kg of wet cells which were 'bagged' and frozen for storage until required.

TABLE 4

| Component | Seed (g/l) | Fermenter (g/l) |
|---|---|---|
| Yeast Extract | 5 | 20 |
| $(NH_4)_2SO_4$ | 1 | 0.1 |
| $MgSO_4.7H_2O$ | 0.1 | 0.1 |
| $KH_2PO_4$ | 5 | 5 |
| Succinic acid | — | 10 |
| $CaCl_2 2H_2O$ | — | 0.05 |
| Trace Element Solution | 0.1 ml/l | 0.1 ml/l |
| XFO371 Antifoam* | — | 0.5 ml/l |
| Adjust to pH 7.0 with NaOH | | |

*Ivanhoe Chem. Co., IL, USA.

EXAMPLE 4
Purification 4.25 kg of wet cells were taken for partial purification of the N-acyl-pipecolic acid acylase activity. The cells were lysed by suspending the cells in 13 l of 10 mM Tris (pH 7.2) plus 5 mM EDTA, adding Lysozyme (Europa 097A50000, Cambridge UK) to 0.2 mg/ml and mixing at room temperature overnight. Following lysis, streptomycin sulphate was added at 2% and mixing continued for a further 30 minutes. The cell debris and DNA precipitate were then removed by centrifugation to leave 16.5 l of clear amino acylase-containing solution. This was reduced in volume to 10.4 l using an Amicon hollow fibre ultrafiltration module containing a membrane with a molecular weight cut-off of 30,000 Da.

The pH was then adjusted to 7.0 by the addition of 1M HCL and the conductivity brought to 10.8 mS by the addition of 65 g KCl. This enzyme solution was then partially purified by anion-exchange chromatography using the cellulose-based support, DE52. The enzyme was loaded batchwise onto 1.6 kg gel then washed twice with 5 column volumes of 10 mM Tris plus 0.1M KCl (pH 7) buffer. The washed gel was then loaded into a column and the protein eluted by a continuous salt gradient between 0.1 KCl and 0.5 KCl (in 10 mM Tris buffer) over 5 column volumes. The main peak of activity was found to elute between 0.2 and 0.3M KCl. The active fractions were then pooled to give an enzyme solution with a specific activity of 1.3 U/mg protein.

Activity in this case was measured using N-acetyl-(R,S)-pipecolic acid as a substrate at 30 g/l in 10 mM potassium phosphate buffer, pH 7. After addition of enzyme to the substrate, the solution was shaken at 25° C. for 1 hour. A sample was taken and then assayed for N-acetyl-pipecolic acid hydrolysis by HPLC using a C18 Hichrom SSODS2 column. 1 unit of activity is defined as the hydrolysis of 1 µmole of substrate in 1 minute under the conditions of the assay.

EXAMPLE 5
Enzyme Immobilisation

In order to maximise the use of an enzyme, it is often desirable to immobilize it onto a support that enables ready separation of the enzyme from the reaction products for re-use, and in some instances, can lead to enzyme stabilization. In this instance, a glutaraldehyde-activated microporous membrane material was obtained from Arbor Technologies Inc (Pine Brook, N.J., USA). The enzyme could be easily immobilised by recycling the enzyme solution over the membrane following the manufacturer's recommendations. This then gives a stable preparation, with the enzyme covalently linked to the support.

To a spiral-wound membrane unit having a nominal protein binding capacity of 4.2, partially purified enzyme solution corresponding to 2.75 g protein and 1960 units of activity was immobilized. Following immobilization, substrate solution at concentrations up to 150 g/l N-acetyl-(R, S)-pipecolic acid in 10 mM potassium phosphate pH 7.0 were pumped in recycle mode over the surface of the membrane. Periodically, the substrate solution was changed after 40–45% conversion of the racemic substrate, and fresh substrate used. The initial expressed activity was observed to be at about 65% of the expected rate based on the amount of enzyme immobilized. Analysis of recovered pipecolic acid from the product broth by chiral HPLC showed it to have an ee>99% for (S)-pipecolic acid.

The activity of the immobilized preparation was monitored over the following 50 days: the activities were similar at the beginning and at the end of this period. During this period there was intermittent washing of the membrane with 10 mM potassium phosphate, pH 7.0 plus % sodium azide, to prevent contaminant growth.

EXAMPLE 6
Alternative substrates

The activity of a semi-purified enzyme preparation, as described in Example 4, was tested on a range of alternative substrates. Various N-acetylamino-acid solutions were prepared at a concentration of 40 g/l in 100 mM Tris buffer at pH 7.5. Reactions were then set up using 1 ml of reaction substrate plus 0.5 ml enzyme plus 0.5 ml 100 mM Tris buffer, pH 7.5. The reaction mixtures were shaken at 24°–25° C. for 1 hour before being analysed for amino-acid formation. Result are shown in Table 5. The extent of reaction for the N-acetylpipecolic acid and N-acetylproline biotransformations was determined using the HPLC methodology described in Example 1. The extent and enantioselectivity of the other biotransformations was determined using a Nucleosil Chiral-1 (ET250/8/4 with a buffer phase of 1 mM copper acetate at pH 5 in 5% methanol, and a flow rate of 0.8 ml/min, with detection at 254 nm. Samples were diluted 100-fold and areas compared to relevant standards.

TABLE 5

| Substrate | Amino-acid formed (g/l) |
|---|---|
| N-acetyl-(R,S)-pipecolic acid | 6.3 |
| N-acetyl-(S)-proline | 3.2 |
| N-acetyl-(R,S)-phenylalanine | 5.3 |
| N-acetyl-(R,S)-4-cyanophenylalanine | 8.3 |
| N-acetyl-(R,S)-alanine | 3.4 |
| N-acetyl-(R,S)-glutamic acid | 0.2 |
| εN-acetyl-(S)-lysine | 0.0 |

Analysis of primary amino-acids formed showed no detectable level of (R)-amino-acid (greater than 98% ee (S)-amino-acid formed). Therefore, the enantioselectivity found for hydrolysis of N-acetylpipecolic acid is also observed for other amino-acids.

The results show that, under the conditions of the assay, the enzyme is more active against N-acetyl-(R,S)-pipecolic acid than against N-acetyl-(S)-proline. Surprisingly, it is also found that the enzyme has good activity with a range of N-acetyl-primary amino-acids as substrates. This is clearly of industrial advantage in that a single enzyme preparation, or immobilized preparation, may be used for resolving a range of amino-acids, both primary (aliphatic and aromatic) and secondary.

The enzyme described in EP-A-0416282, for instance, has non-detectable activity against N-acetyl-(R,S)-alanine or N-acetyl-(R,S)-phenylalanine.

EXAMPLE 7

Alternative buffers

The acylase disclosed in EP-A-0416282 is inhibited by reaction in buffers containing phosphate at high concentrations. The effect of high phosphate on the biotransformation was determined using a similar methodology to that described in Example 6. Results are shown in Table 6.

TABLE 6

| Buffer | Substrate | Amino-acid formed (g/l) |
|---|---|---|
| 100 mM Phosphate, pH 7.5 | N-acetyl-(R,S)-pipecolic acid | 6.3 |
| 100 mM Phosphate, pH 7.5 | N-acetyl-(S)-proline | 3.2 |
| 100 mM Tris, pH 7.5 | N-acetyl-(R,S)-pipecolic acid | 6.3 |
| 100 mM Tris, pH 7.5 | N-acetyl-(S)-proline | 3.2 |

Results show that phosphate has no significant inhibitory effect on the amino acylase. (The final phosphate concentration is calculated to be equal to or greater than 75 mM).

We claim:

1. A process for preparing (S)-pipecolic acid, which comprises contacting a mixture of enantiomers of a N-acylpipecolic acid with an enzyme having acylase activity capable of hydrolyzing N-acetyl-(R,S)-pipecolic acid stereoselectively to give (S)-pipecolic acid, wherein said activity is greater than that on N-acetyl-S-proline, at pH 7.5, 25° C., and substrate concentration 20 g/l, in 75 mM Tris buffer, and obtainable from the species of Alcaligenes denitrificans deposited as NCIMB 40587, or with a microorganism capable of hydrolyzing N-acetyl-(R,S)-pipecolic acid stereoselectively to give (S)-pipecolic acid, by virtue of having therein an enzyme having acylase activity capable of hydrolyzing N-acetyl-(R,S)-pipecolic acid stereoselectively to give (S)-pipecolic acid, wherein said activity is greater than that on N-acetyl-S-proline, at pH 7.5, 25° C. and substrate concentration 20 g/l, in 75 mM Tris buffer, and having the characteristics of the microorganism deposited as NCIMB 40587.

2. A process according to claim 1, wherein said N-acylpipecolic acid is N-acetylpipecolic acid.

3. A process according to claim 2, wherein the product is obtained in at least 95% ee.

4. A process according to claim 3, wherein said ee is more than 98%.

5. A process according to claim 1, wherein the product is obtained in at least 95% ee.

6. A process according to claim 5, where said ee is more than 98%.

7. A process according to claim 1, wherein said enzyme is used.

8. A process according to claim 7, wherein said enzyme is immobilized.

9. A process according to claim 1, wherein said microorganism is used.

10. An isolated microorganism capable of hydrolyzing N-acetyl-(R,S)-pipecolic acid stereoselectively to give (S)-pipecolic acid, by virtue of having therein an enzyme having acylase activity capable of hydrolyzing N-acetyl-(R,S)-pipecolic acid stereoselectively to give (S)-pipecolic acid, wherein said activity is greater than that on N-acetyl-S-proline, at pH 7.5, 25° C. and substrate concentration 20 g/l, in 75 mM Tris buffer, and having the characteristics of the microorganism deposited as NCIMB 40587.

11. An isolated enzyme having acylase activity capable of hydrolyzing N-acetyl-(R,S)-pipecolic acid stereoselectively to give (S)-pipecolic acid, wherein said activity is greater than that on N-acetyl-S-proline, at pH 7.5, 25° C., and substrate concentration 20 g/l, in 75 mM Tris buffer, and obtainable from the species of Alcaligenes denitrificans deposited as NCIMB 40587.

* * * * *